United States Patent [19]

Calderazzo et al.

[11] Patent Number: 5,093,508
[45] Date of Patent: Mar. 3, 1992

[54] PROCESS FOR PRODUCING VANADIUM-ARENES

[75] Inventors: Fausto Calderazzo, Ghezzamo; Guido Pampaloni, Pontedera; Lucia Rocchi, Livorno; Angelo Moalli, Castelletto Ticino; Francesco Masi, San Donato Milanese; Renzo Invernizzi, Milan, all of Italy

[73] Assignee: Enimont Anic S.r.l., Palermo, Italy

[21] Appl. No.: 641,877

[22] Filed: Jan. 4, 1991

[30] Foreign Application Priority Data

Jan. 19, 1990 [IT] Italy ................ 19111 A/90

[51] Int. Cl.$^5$ ................ C07F 9/00
[52] U.S. Cl. ................ 556/43; 556/42
[58] Field of Search ................ 556/43, 42

[56] References Cited

U.S. PATENT DOCUMENTS 4,526,724  7/1985  Pillsbury ................ 556/43
4,980,491 12/1990  Calderazzo et al. ................ 556/43

Primary Examiner—Arthur C. Prescott
Attorney, Agent, or Firm—Shea & Gould

[57] ABSTRACT

Vanadium-arenes $$[V(arene)_2]$$

wherein "arene" means benzene or mono-, di- or poly-($C_1$-$C_5$)-alkyl-substituted benzene, are prepared by means of a process which comprises:
(a) forming a complex:

$$[V(arene)_2](+).AlCl_4(-)$$

by reacting vanadium trichloride, aluminum metal and aluminum trichloride with one another, by operating in the presence of the selected arene;
(b) treating the so obtained complex with an either cyclic or acyclic, liquid aliphatic ether to obtain the reduction of $[V(arene)_2](+)$ to $[V(arene)_2]$; and
(c) recovering the so separated vanadium-arene.

The vanadium-arenes are useful in the preparation of catalysts for olefin polymerization.

10 Claims, No Drawings

PROCESS FOR PRODUCING VANADIUM-ARENES

The present invention relates to an improved process for producing vanadium-arenes.

Vanadium-arenes are compounds useful in the art, in particular for preparing catalysts for olefin polymerization.

Thus, according to U.S. patent application Ser. No. 403,681 filed on Sept. 6, 1989, now U.S. Pat. No. 4,987,111 a solid catalyst component is obtained by reaction between a vanadium-arene

[V(arene)$_2$]

and titanium tetrachloride. Such a catalyst component, together with a trialkyl-aluminum, is highly active in ethylene polymerization, or in the copolymerization of ethylene with a $C_3$-$C_{10}$ alpha-olefin, in the processes carried out in suspension under low pressure and at low temperature, in the high-pressure, high-temperature processes carried out inside tubular reactors or vessels, and in the high-temperature processes carried out in solution.

Processes for preparing vanadium-arenes are known in the art. Among them there are those described by E. O. Fischer and H. S. Kogler in Chem. Ber. 90 250 (1957) and by F. Calderazzo in Inorg. Chem. 3 810 (1964). These are anyway processes which enable very low—therefore not attractive from the commercial view point—yields of useful reaction products to be obtained (overall yields of the order of 15%).

In U.S. patent application Ser. No. 516,267 filed on Apr. 30, 1990, now U.S. Pat. No. 4,980,491 a process for producing vanadium-arenes is disclosed, which comprises reducing a vanadium-arene iodide with particular reducing agents belonging to the classes of metals or organometallic compounds. In its turn, vanadium-arene iodide can be obtained by reacting vanadium chloride with aluminum metal and aluminum trichloride to yield a complex:

[V(arene)$_2$](+).AlCl$_4$(−)

subsequently treating this complex with an alkali-metal iodide. By operating according to the process disclosed in the above cited patent application, vanadium-arenes can be obtained with overall yields of about 50%.

The present Applicant has found now according to the present invention that vanadium-arenes can be prepared by means of a simple, advantageous process easily applied at the commercial level which, at least under the preferred conditions, makes it possible high reaction yields to be obtained.

In accordance with the above, the present invention relates to a process for producing vanadium-arenes

[V(arene)$_2$]

wherein "arene" means benzene or mono-, di- or poly-($C_1$-$C_5$)-alkyl-substituted benzene, in which
(a) a complex:

[V(arene)$_2$](+).AlCl$_4$(−)

is prepared by reacting vanadium trichloride, aluminum metal and aluminum trichloride in the presence of the selected arene;
(b) the so obtained complex is treated with an either cyclic or acyclic, liquid aliphatic ether to obtain the reduction of [V(arene)$_2$](+) to [V(arene)$_2$]; and
(c) the so separated vanadium-arene is recovered.

The reaction of formation of vanadium-arenes according to the present invention can be schematically shown as follows:

$$3\ VCl_3 + 2Al + AlCl_3 + 2\ arene \longrightarrow$$

$$3\ [V(arene)_2](+).AlCl_4(-)$$

$$3\ [V(arene)_2](+).AlCl_4(-) + Al + 4n\ ether \longrightarrow$$

$$3\ V(arene)_2 + 4\ AlCl_3.n\ ether$$

In the (a) step of the process according to the present invention vanadium trichloride, aluminum metal, aluminum trichloride and an arene are brought into contact with one another under reaction conditions. Examples of arenes suitable for the intended purpose are benzene, toluene, p-xylene and mesitylene. Among these, mesitylene is preferred.

The reaction is advantageously carried out with a molar ratio of aluminum trichloride to vanadium trichloride comprised within the range of from 0.33:1 to 2:1, with a molar ratio of arene to vanadium trichloride comprised within the range of from 2:1 to 10:1 and with a ratio of the atoms of aluminum metal to the moles of vanadium trichloride comprised within the range of from 1:1 to 5:1. The best results are obtained when the reaction is carried out with a molar ratio of aluminum trichloride to vanadium trichloride comprised within the range of from 1:1 to 2:1, with a molar ratio of arene to vanadium trichloride comprised within the range of from 4:1 to 10:1 and with a ratio of the atoms of aluminum metal to the moles of vanadium trichloride comprised within the range of from 1:1 to 2:1. Furthermore, in said (a) step the reaction is carried out at a temperature comprised within the range of from 100° C. to 130° C. and for a time of from 2 to 4 hours. The preferred values of temperature and reaction time are of from 120° C. to 130° C., and of from 2 to 3 hours, respectively.

In the (b) step of the process of the present invention an either cyclic or acyclic aliphatic, liquid ether is added to the reaction product from the (a) step. Useful ethers for the intended purpose are tetrahydrofuran, diethyl ether, dimethoxy-ethane, diethylene glycol dimethyl ether. Of these, tetrahydrofuran is preferred. The amount of ether added is not critical; however, amounts of ether of from 100 to 200 parts by weight per each 100 parts by weight of reaction mixture are normally useful for the intended purpose. During this reaction step, a diluent, preferably a hydrocarbon diluent, liquid under the operating conditions, and preferably a saturated aliphatic hydrocarbon diluent, such as, e.g., n-heptane, may be added to the reaction. The treatment with the ether can take place at a temperature comprised within the range of from 0° C. to 50° C., but the reaction is preferably carried out at room temperature (20°-25° C.). As a general rule, the contact times may range from 2 to 48 hours, and will preferably be of the order of from 2 to 5 hours.

In the (c) step of the process according to the present invention, the vanadium-arene obtained in the (b) step can be separated from the reaction mixture by the normal separation techniques. For examples, one might operate by evaporating off the ether and the possibly present hydrocarbon diluent from the reaction mixture. The distillation residue can be subsequently treated with a solvent capable of dissolving the vanadium-arene, such as, e.g., a hydrocarbon solvent, in particular an aliphatic hydrocarbon solvent, such as n-heptane. The so obtained solution can be separated from any reaction byproducts in the solid state by filtration or centrifugation. The vanadium-arene can be then recovered from this solution by evaporating the solvent, or by crystallization caused by cooling the solution to a low temperature, and/or by adding a non-solvent.

The so obtained vanadium-arenes are solid products having melting points comprised within the range of from 100° C. to 300° C. These vanadium-arenes can be reacted with titanium tetrachloride to prepare solid catalyst components which, together with a trialkyl-aluminum, are highly active in the polymerization of ethylene or in the copolymerization of ethylene with a $C_3$-$C_{10}$ alpha-olefin, in the processes carried out in suspension under low pressure and at low temperature, in the high-pressure, high-temperature processes carried out inside tubular reactors or vessels, and in the high-temperature processes carried out in solution.

The following experimental examples are reported for the purpose of illustrating the invention in greater detail.

EXAMPLE 1

A mixture of vanadium trichloride (5 g, 31.7 mmol), aluminum powder (0.855 g, 31.7 mmol), aluminum trichloride (1.42 g, 10.6 mmol) and 9.1 ml (63.5 mmol) of mesitylene is charged to a glass flask equipped with a thermometer, stirrer and dropping funnel.

The mixture is heated to 130° C. and is kept at this temperature for 2 hours and a suspension having an intense red-brown colour is obtained. The suspension is cooled to room temperature (20°-25° C.) and 10 ml of n-heptane and 70 ml of anhydrous tetrahydrofuran are added. The resulting mixture is kept with strong stirring for 2 hours. The mixture is then concentrated to dryness (0.1 torr, 50° C.) and the solid residue is suspended again in anhydrous n-heptane (130 ml).

The suspension is filtered and a clear solution of red-brown colour is obtained, which contains 3.87 g (13.3 mmol) of vanadium-bis-(mesitylene)

[V(mesitylene)$_2$]

The yield is of 42%, expressed as moles referred to the moles of initially charged vanadium trichloride.

EXAMPLE 2

A mixture of vanadium trichloride (5 g, 31.7 mmol), aluminum powder (1.71 g, 63.3 mmol), aluminum trichloride (1.42 g, 10.6 mmol) and 18.2 ml (127 mmol) of mesitylene is charged to a glass flask equipped with a thermometer, stirrer and dropping funnel.

The mixture is heated to 130° C. and is kept heated at this temperature for 2 hours and a suspension having an intense red-brown colour is obtained. The suspension is cooled to room temperature (20°-25° C.) and 10 ml of n-heptane and 70 ml of anhydrous tetrahydrofuran are added. The resulting mixture is kept with strong stirring for 3 hours. The mixture is then concentrated to dryness (0.1 torr, 50° C.) and the solid residue is suspended again in anhydrous n-heptane (50 ml).

The suspension is filtered and a clear solution of red-brown colour is obtained, which contains 3.87 g (13.3 mmol) of vanadium-bis-(mesitylene)

[V(mesitylene)$_2$]

The yield is of 42%, expressed as moles referred to the moles of initially charged vanadium trichloride.

EXAMPLE 3

A mixture of vanadium trichloride (5 g, 31.7 mmol), aluminum powder (1.71 g, 63.3 mmol), aluminum trichloride (4.22 g, 31.7 mmol) and 18.2 ml (127 mmol) of mesitylene is charged to a glass flask equipped with a thermometer, stirrer and dropping funnel.

The mixture is heated to 130° C. and is kept heated at this temperature for 2 hours and a suspension having an intense red-brown colour is obtained. The suspension is cooled to room temperature (20°-25° C.) and 10 ml of n-heptane and 60 ml of anhydrous tetrahydrofuran are added. The resulting mixture is kept with strong stirring for 3 hours. The mixture is then concentrated to dryness (0.1 torr, 50° C.) and the solid residue is suspended again in anhydrous n-heptane (60 ml).

The suspension is filtered and the solid is washed with n-heptane. A total volume of 127 ml of a clear solution of red-brown colour is obtained, which contains 8.3 g (28.5 mmol) of vanadium-bis-(mesitylene)

[V(mesitylene)$_2$]

The yield is of 90%, expressed as moles referred to the moles of initially charged vanadium trichloride.

EXAMPLE 4

A mixture of vanadium trichloride (58.2 g, 0.37 mol), aluminum powder (10 g, 0.37 mol), aluminum trichloride (70 g, 0.52 mol) and 317 ml (2.22 mol) of mesitylene is charged under a blanketing nitrogen atmosphere to a large glass test tube of 0.5 liters of capacity, with side fitting.

The mixture is heated to a temperature of 120°-130° C. and is kept heated at this temperature for 2 hours. A suspension having an intense red-brown colour is obtained. The suspension is cooled to room temperature (20°-25° C.) and 50 ml of n-heptane and 300 ml of anhydrous tetrahydrofuran are added. The resulting mixture is kept with strong stirring for 5 hours. The mixture is then concentrated to dryness (0.1 torr, 50° C.) and the solid residue is suspended again in anhydrous n-heptane (60 ml).

The suspension is filtered and the solid is washed with n-heptane. A total volume of 400 ml of a clear solution of red-brown colour is obtained. This solution is concentrated again to dryness and 70 g of vanadium-bis-(mesitylene)

[V(mesitylene)$_2$]

is obtained. The yield is of 65%, expressed as moles referred to the moles of initially charged vanadium trichloride.

EXAMPLE 5

A mixture of vanadium trichloride (4.6 g, 29 mmol), aluminum powder (1.6 g, 59 mmol), aluminum trichloride (7.8 g, 58 mmol) and 40 ml (279 mmol) of mesitylene is charged under a blanketing nitrogen atmosphere to a large glass test tube of 0.5 liters of capacity, with side fitting.

The mixture is heated to a temperature of 120°–130° C. and is kept heated at this temperature for 2 hours. A suspension having an intense red-brown colour is obtained. The suspension is cooled to room temperature (20°–25° C.) and 70 ml of n-heptane and 70 ml of anhydrous tetrahydrofuran are added. The resulting mixture is kept with strong stirring for 48 hours. The mixture is then concentrated to dryness (0.1 torr, 50° C.) and the solid residue is suspended again in anhydrous n-heptane (100 ml).

The suspension is filtered and the so obtained clear solution is concentrated to an end volume of 50 ml, is cooled to −78° C. and is kept cooled overnight at this temperature. 6.53 g of vanadium-bis-(mesitylene)

[V(mesitylene)$_2$]

is recovered. The yield is of 77%, expressed as moles referred to the moles of initially charged vanadium trichloride.

We claim:

1. Process for producing vanadium-arenes

[V(arene)$_2$]

wherein "arene" means benzene or mono-, di- or poly-(C$_1$-C$_5$)-alkyl-substituted benzene, characterized in that:
   (a) a complex:

[V(arene$_2$)(+).AlCl$_4$(−)]

is formed ting vanadium trichloride, aluminum metal and aluminum trichloride with another one in the presence of the selected arene;
   (b) the so obtained complex is treated with an either cyclic or acyclic, liquid aliphatic ether to obtain the reduction of [V(arene)$_2$](+) to [V(arene)$_2$]; and
   (c) the so separated vanadium-arene is recovered.

2. Process according to claim 1, characterized in that the arene is selected from among benzene, toluene, p-xylene and mesitylene and preferably is mesitylene.

3. Process according to claim 1, characterized in that in the (a) step the reaction is carried out with a molar ratio of aluminum trichloride to vanadium trichloride comprised within the range of from 0.33:1 to 2:1, with a molar ratio of arene to vanadium trichloride comprised within the range of from 2:1 to 10:1 and with a ratio of the atoms of aluminum metal to the moles of vanadium trichloride comprised within the range of from 1:1 to 5:1.

4. Process according to claim 3, characterized in that in said (a) step the reaction is carried out with a molar ratio of aluminum trichloride to vanadium trichloride comprised within the range of from 1:1 to 2:1, with a molar ratio of arene to vanadium trichloride comprised within the range of from 4:1 to 10:1 and with a ratio of the atoms of aluminum metal to the moles of vanadium trichloride comprised within the range of from 1:1 to 2:1.

5. Process according to claim 1, characterized in that in said (a) step the reaction is carried out at a temperature comprised within the range of from 100° C. to 130° C. and for a time of from 2 to 4 hours.

6. Process according to claim 5, characterized in that in said (a) step the values of temperature and reaction time are of from 120° C. to 130° C., and of from 2 to 3 hours, respectively.

7. Process according to claim 1, characterized in that in the (b) step an either cyclic or acyclic aliphatic, liquid ether is added to the reaction product from the (a) step in an amount of from 100 to 200 parts by weight per each 100 parts by weight of reaction mixture, by operating at a temperature comprised within the range of from 0° C. to 50° C. and preferably at room temperature (20°–25° C.), for a contact time of from 2 to 48 hours, and preferably of the order of from 2 to 5 hours.

8. Process according to claim 7, characterized in that in said (b) step the ether is selected from the group consisting of tetrahydrofuran, diethyl ether, dimethoxyethane, diethylene glycol dimethyl ether, and preferably is tetrahydrofuran.

9. Process according to claim 8, characterized in that in said (b) step the process is carried out in the presence of a liquid hydrocarbon diluent and preferably in the presence of a saturated aliphatic hydrocarbon diluent.

10. Process according to claim 1, characterized in that in the (c) step the ether and the possibly present hydrocarbon diluent is evaporated off from the reaction mixture coming from the (b) step, and the evaporation residue is treated with a solvent for vanadium-arene, such as to obtain a solution of vanadium-arene in said solvent, and vanadium-arene is separated from this solution by evaporating the solvent, or by crystallization caused by a temperature decrease, and/or addition of a non-solvent.

* * * * *

UNITED STATES PATENT AND TRADEMARK OFFICE
CERTIFICATE OF CORRECTION

PATENT NO. : 5,093,508

DATED : March 3, 1992

INVENTOR(S) : Fausto Calderazzo, Guido Pampaloni, Lucia Rocchi, Angelo Moalli, Francesco Masi and Renzo Invernizzi It is certified that error appears in the above-identified patent and that said Letters Patent is hereby corrected as shown below:

Column 5, in Claim 1, in line 7, the formula "[V(arene$_2$](+) .AlCl$_4$(-)" should read as --[V(arene)$_2$](+)·AlCl$_4$(-)--;

In Claim 1, in line 8, the word "ting" should not appear; and

In Claim 1, in line 8, after the word "formed" and before the word "vanadium", the words --by reacting-- should be inserted.

Signed and Sealed this

Fourteenth Day of September, 1993

Attest:

BRUCE LEHMAN

Attesting Officer     Commissioner of Patents and Trademarks